(12) United States Patent
Beisang, III et al.

(10) Patent No.: US 8,838,228 B2
(45) Date of Patent: Sep. 16, 2014

(54) SYSTEMS AND METHODS FOR REDUCING THE PROLIFERATION OF MICROORGANISMS

(76) Inventors: Arthur Beisang, III, North Oaks, MN (US); Andrew Kirchoff, White Bear Lake, MN (US); David Shelander, Roseville, MN (US)

( * ) Notice: Subject to any disclaimer, the term of this patent is extended or adjusted under 35 U.S.C. 154(b) by 203 days.

(21) Appl. No.: 13/228,592

(22) Filed: Sep. 9, 2011

(65) Prior Publication Data
US 2012/0265120 A1    Oct. 18, 2012

Related U.S. Application Data

(60) Provisional application No. 61/476,190, filed on Apr. 15, 2011.

(51) Int. Cl.
A61N 1/30    (2006.01)
A61N 5/06    (2006.01)

(52) U.S. Cl.
CPC ....... *A61N 5/0624* (2013.01); *A61N 2005/0643* (2013.01); *A61N 2005/0662* (2013.01); *A61N 5/0616* (2013.01)
USPC ......................................................... 604/20

(58) Field of Classification Search
USPC .......................................................... 604/20
See application file for complete search history.

(56) References Cited

U.S. PATENT DOCUMENTS

| | | |
|---|---|---|
| 3,557,783 A | 1/1971 | Castner |
| 4,305,390 A | 12/1981 | Swartz |
| 4,778,456 A | 10/1988 | Lokken |
| 4,996,046 A | 2/1991 | Warshaw et al. |
| 5,236,421 A | 8/1993 | Becher |
| 5,260,020 A | 11/1993 | Wilk et al. |
| 5,445,608 A | 8/1995 | Chen et al. |
| 5,480,647 A | 1/1996 | Tsai |
| 5,709,653 A | 1/1998 | Leone |
| 5,769,807 A | 6/1998 | Haddock et al. |
| 5,855,570 A | 1/1999 | Scherson et al. |
| 5,871,522 A | 2/1999 | Sentilles |
| 6,283,986 B1 | 9/2001 | Johnson |
| 6,461,569 B1 | 10/2002 | Boudreaux |
| 6,730,113 B2 * | 5/2004 | Eckhardt et al. ................ 607/94 |
| 6,800,064 B2 | 10/2004 | Liang |
| 7,137,968 B1 | 11/2006 | Burrell et al. |
| 7,304,201 B2 | 12/2007 | Holloway et al. |
| 7,335,376 B2 | 2/2008 | Vorozhtsov et al. |
| 7,507,228 B2 | 3/2009 | Sun et al. |
| 7,686,839 B2 * | 3/2010 | Parker ............................ 607/93 |
| 8,128,672 B2 | 3/2012 | Quisenberry et al. |
| 2002/0173833 A1 | 11/2002 | Korman et al. |
| 2004/0010299 A1 * | 1/2004 | Tolkoff et al. .................. 607/88 |
| 2004/0039242 A1 | 2/2004 | Tolkoff et al. |
| 2007/0176117 A1 | 8/2007 | Redmond et al. |
| 2008/0051736 A1 | 2/2008 | Rioux et al. |

* cited by examiner

*Primary Examiner* — Kevin C Sirmons
*Assistant Examiner* — Deanna K Hall
(74) *Attorney, Agent, or Firm* — Underwood & Associates, LLC (57) ABSTRACT

Systems and methods are provided that reduce the likelihood of infection caused by microorganisms. In general, microorganism population control can be achieved by exposing the population to an effective dose of electromagnetic radiation sufficient to cause a reduction in proliferation of the microorganism, wherein the electromagnetic radiation has a center wavelength between about 385 nm and about 425 nm. In preferred embodiments, the systems and methods described herein can be embodied in catheterization systems.

18 Claims, 12 Drawing Sheets

SYSTEMS AND METHODS FOR REDUCING THE PROLIFERATION OF MICROORGANISMS

CROSS REFERENCE TO RELATED APPLICATIONS

This application claims priority under 35 U.S.C. §119(e) of U.S. Patent Application No. (USPN) 61/476,190, filed Apr. 15, 2011 by Arthur Allen Beisang, David John Shelander, and Andrew John Kirchoff, entitled "Method and Apparatus for Sterilizing or Disinfecting Mammalian Tissues and Catheters Using Wavelengths of Light in the Violet Range." USPN 61/476,190 is hereby incorporated by reference in its entirety as if fully set forth herein.

STATEMENT REGARDING FEDERALLY SPONSORED RESEARCH OR DEVELOPMENT

None.

TECHNICAL FIELD

This disclosure relates to systems and methods for reducing the likelihood of infections caused by microorganisms. In particular, this disclosure relates to systems, articles, and methods for reducing the likelihood of nosocomial infections using an effective dose of electromagnetic radiation in a preferred range of predominant (center) wavelengths.

BACKGROUND

Infection is a primary concern in healthcare settings. Nosocomial infections are infections that originate in a hospital or a healthcare service unit, often the result of infectious microorganisms entering the body through open wounds, skin lesions or incisions, or mucous membranes. Microorganisms including harmful bacteria can cause infections in the body when they traverse the protective layers of the skin. There can be increased susceptibility to infection where skin ulceration exists or where the dermal layers are breached, such as catheter insertion sites in skin. When infections occur, they can cause significant morbidity and mortality thus increasing both the cost of healthcare and the length of hospitalization.

Catheters are placed into the body for many reasons. It is well known in the medical arts that the skin or other entrance points must be thoroughly disinfected prior to the introduction of any catheter, e.g., through the skin. It is also common practice to place a sterile, adhesive flexible membrane over the catheter insertion site to further protect against microorganism infection at the catheter entry site. It can be difficult, however, to maintain sterility at catheter insertion sites over a length of time. Despite ongoing infection prevention and intervention measures, nosocomial infections originating from catheterization procedures remain a serious healthcare problem.

Some infection prevention measures include completely changing the overlying catheter dressings and disinfecting the insertion site with chemical disinfectants or sterilizing agents. These procedures can increase the chances of dislodging the underlying catheter, however, and can additionally cause harm to the skin and blood vessels. Furthermore yet, some patients react unfavorably to chemical disinfectants through allergic reactions or irritation.

SUMMARY

In one general aspect, a system for reducing the likelihood of infection in a living system is provided. The system includes a light source capable of producing an effective dose of electromagnetic radiation so as to reduce the proliferation of microorganisms on a target surface, where the electromagnetic radiation has a center wavelength between about 385 nm and about 425 nm. The system further includes a protective dressing configured to cover all, or a portion of the target surface, where the dressing includes a window that is substantially transparent to the electromagnetic radiation.

In one embodiment, the microorganisms are one or more of: bacteria, fungi, or protist.

In one embodiment, the system further includes a support body capable of securing the light source proximate to the target surface in an orientation suitable to project the electromagnetic radiation through the dressing and onto the target surface. In one embodiment, the target surface is a selected portion of skin, tissue, bone, muscle fiber, lumen, or organ.

In one embodiment, the protective covering includes a clear acrylic substrate and an adhesive layer configured to adhere the protective covering to the target surface.

In one embodiment, the dressing includes one or more layers of a solid, liquid, or gel material.

In one general aspect, a system for reducing the likelihood of infection caused by catheterization is provided. The system includes a light source capable of producing an effective dose of electromagnetic radiation sufficient to reduce proliferation of a population of infectious microorganisms, where the electromagnetic radiation has a center wavelength between about 385 nm and about 425 nm. The system further includes optical components and support structures for projecting the electromagnetic radiation onto, and adjacent a catheter insertion site, where a catheter is inserted into a body part of a living system.

In one embodiment, the means for projecting the radiation onto, and adjacent the incision site includes one or more waveguides configured to carry the electromagnetic radiation from a distal end to a proximal end of the catheter. The distal end of the waveguide is configured to receive the output of the light source, and the proximal end is configured to project the electromagnetic radiation onto the incision site.

In one embodiment, the waveguide is embedded in a catheter having a central bore for transporting fluids into and out of the living system.

In one embodiment, the system further includes a protective dressing configured to reversibly hold the projecting means proximate to the catheter insertion site.

In one embodiment, the protective dressing is one or more of a solid, liquid, or gel dressing.

In one embodiment, the system further includes a control module configured to allow user input for controlling one or more of exposure time, exposure intensity, and time between repeated exposures of the electromagnetic radiation.

In one general aspect, a method for reducing the likelihood of infection in a living system is provided. The method includes providing a light source capable of producing an effective dose of electromagnetic radiation sufficient to cause a reduction in proliferation of a microorganism. The light source has a center wavelength between about 385 nm and about 425 nm. The method further includes providing a dressing for covering an exposure area that is susceptible to infection through the presence of the microorganisms. The method further includes projecting the electromagnetic radiation through the dressing, and onto the exposure area in an effective dose sufficient to reduce the proliferation of the microorganisms.

In one embodiment, the light source includes a laser, diode, excitable gas, or filament.

In one embodiment, the exposure area is a catheter insertion site, where a catheter has been introduced into the living system. In one embodiment, the exposure area includes skin of the living system.

In one embodiment, the dressing is one or more of a solid, liquid or gel dressing that is substantially transparent to the electromagnetic radiation.

In one embodiment, projecting the electromagnetic radiation through the dressing includes projecting the output of the light source toward the dressing; or carrying the output of the light source to an area proximate to the exposure area through the use of one or more waveguides, and directing an output end of the waveguide onto the dressing so as to irradiate the exposure area with the electromagnetic radiation.

In one embodiment, the exposure area receives a plurality of effective doses over a selected period of time to further prevent colonization of the microorganisms.

In one embodiment, the effective dose is determined based on the type of microorganism(s) on or near the exposure area.

Certain advantages of the systems and methods described herein include: a non-invasive treatment method for reducing the likelihood of nosocomial and other infections; reduction of undesirable microorganism population in and around a catheter insertion site without the use of sterilizing agents and other chemicals, or ultra-violet radiation, which has been shown to cause skin cancer; a catheterization system that does not require frequent dressing changes; and the ability to protect against infection from different types of undesirable microorganism populations with a single system; among others.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, and in which.

DETAILED DESCRIPTION OF ILLUSTRATIVE EMBODIMENTS

In general, systems, articles, and methods are disclosed for reducing the likelihood of infection resulting from undesirable microorganism growth in, or on living systems, or on equipment that comes into contact with living systems. The term "microorganism," as used herein, generally refers to microscopic organisms such as bacteria, fungi, protists, and other microorganisms capable of multiplying or colonizing to cause an infection in a host. It will be understood, however, that the systems and methods described herein for reducing the likelihood of infection from these organisms can also be applied for controlling, preventing, or reducing the likelihood of infections from viruses. "Microorganism growth," as used herein, generally refers to an increase in a population of microorganisms.

Nosocomial infections (infections originating in a hospital) are an increasing primary care concern because of the risk of further illness to the patient. The likelihood of developing an infectious disease generally increases when a pathogen enters a body through mucous membranes, inhalation, or when skin is pierced, often times providing a direct route for pathogens to enter the blood stream. In many living systems, the skin is a primary barrier for preventing infection and disease by foreign substances.

Catheters are used in hospitals, ambulances, triage units, and even in battlefields as a way to rapidly introduce fluids, medicines, and other agents directly into a patient's bloodstream or other parts of the body. Catheters are often used in providing intravenous (IV) therapy to patients by accessing veins and arteries in the arms and legs, for example. In many cases, the benefits of this direct access into the body outweigh certain health risks, which include, among others, risk of infection. Even when proper sterilization techniques are performed prior to insertion of a catheter, there is a risk of microorganism growth in the insertion area which provides a direct route for infectious agents to enter the body.

In one general aspect, the likelihood of microorganism growth can be reduced around a catheter insertion site by irradiating the area with electromagnetic radiation, i.e., light, having a center wavelength between about 385 nanometers (nm) and about 425 nm. As used herein, the term "center wavelength" refers to a peak emission wavelength of a given color of light. For example, some laser light has a bandwidth that includes wavelengths of light on low- or high-energy sides (i.e., red-shifted or blue-shifted, respectively) of the predominant color of the light.

Figure 1:
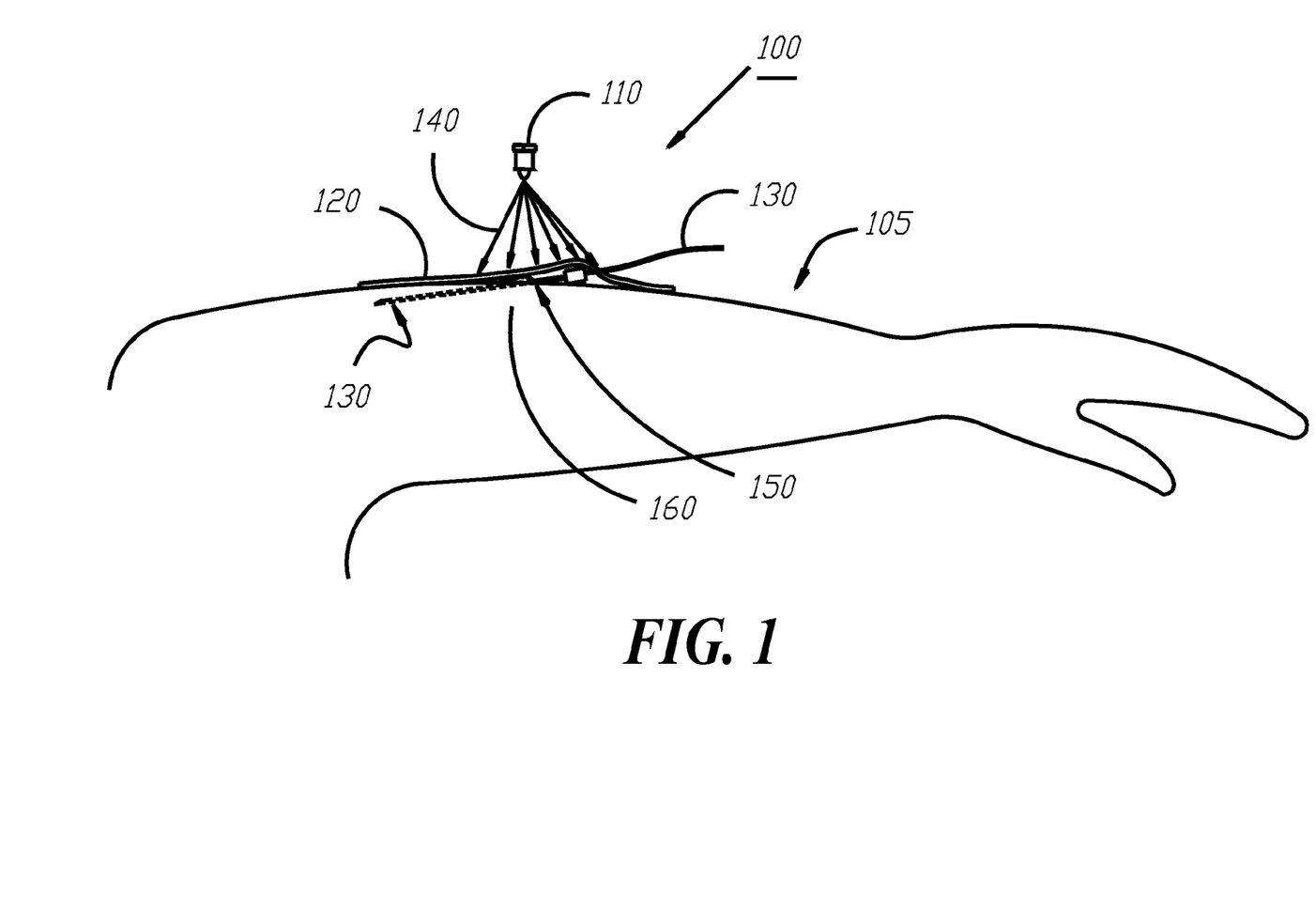
FIG. 1 shows a system for reducing the likelihood of infection, according to one embodiment.

Referring now to FIG. 1, a system 100 for reducing the likelihood of infection is shown, according to one embodiment. In this embodiment, a patient's left arm 105 is shown;

inserted into the arm 105 is a catheter 130. The portion of the catheter 130 shown as a solid line in FIG. 1 exists outside of the arm, while the dashed portion indicates the portion of the catheter within the body, i.e., under the skin 160. The catheter 130 is shown inserted through an insertion site 150 in the arm 105 which can be, e.g., an incision or a break in the skin's continuity from insertion of a needle, and a dressing 120 is shown covering both the insertion site 150 and a portion of the exterior-exposed catheter.

The dressing 120 can be any type of bandage, adhesive, or covering used for reducing the risk of infection in patients. Common dressings for this purpose include, not by way of limitation, absorbent acrylic, hydrocolloid, hydrogel, foam, transparent films, and composites, among others. Those skilled in the art will appreciate that hospitals, health care clinics, ambulance services, and other health care providers often use a wide array of dressings for this particular purpose. In one preferred embodiment, the dressing 120 is an absorbent clear acrylic dressing sold under the Tegaderm brand, produced by 3M Skin and Wound Care Division, 3M Corporation, St. Paul, Minn., USA. Such a dressing usually includes a transparent or translucent sheet of acrylic with an adhesive ring disposed about the periphery of the sheet that adheres to the patient's skin to keep the dressing in place. The transparent or translucent sheet allows heath care providers to monitor a catheter while minimizing the disturbance that can otherwise be caused by frequent dressing changes. In another preferred embodiment, the dressing 120 includes a substantially sterile transparent or semi-transparent film configured to reduce or prevent the introduction of microorganisms to the insertion site 150. An integral adhesive can surround the film about its periphery to adhere the film to the patient's skin. One exemplary dressing of this type is sold under the Sorbaview brand by Centurion Medical Products Corporation, Williamston, Mich., United States.

The catheter 130 can be any type of tube, lumen, or cannula used for introducing substances to, or removing fluids or other substances from a body. Exemplary catheters include those used for intravenous therapy, and those configured to be inserted into a body cavity, duct, or vessel to allow drainage (e.g., in the case of a urinary catheter), to administer fluids, or provide access by surgical instruments to internal body parts e.g., in the practice of angioplasty or endoscopy. The catheter 130 can be a temporary catheter, i.e., an "indwelling" catheter or a permanent catheter generally referred to as a "permcath" and may be flexible or rigid depending on the needs of the patient and the treatment plan of the caregiver.

In this embodiment and all other embodiments described herein, the likelihood of developing an infection as a result of catheterization can be reduced by irradiating the insertion site 150 and the surrounding area with an effective dose of light having a center wavelength of between about 385 nm and about 425 nm, e.g., light having a center wavelength of 385 nm, 390 nm, 395 nm, 400 nm, 401 nm, 402 nm, 403 nm, 404 nm, 405 nm, 406 nm, 407 nm, 408 nm, 409 nm, 410 nm, 415 nm, 420 nm, or 425 nm. In general, and without wishing to be bound by theory, it is believed that an effective dose of light in the wavelength range of between about 385 nm and about 425 nm (hereinafter referred to as "violet" light) causes either microorganism death, or a disruption in microorganism reproduction, or both, and thus can be used as an "antimicrobial" agent, in the sense that it can reduce proliferation of microorganisms.

In preferred embodiments, the light source 110 is capable of emitting light with a center wavelength of about 405 nm. Exemplary light sources 110 for this purpose include, not by way of limitation, lasers, diodes, excitable gases or filaments, and other light sources. In this and all other embodiments, the light source 110 can be configured, including using lenses, windows, filters, and any optics necessary, so as to deliver violet light to a selected treatment area in an effective dose capable of reducing or preventing the proliferation of microorganisms.

In one embodiment, a light source 110 capable of producing or transmitting light radiation (indicated by reference numeral 140 in FIG. 1) in the aforedescribed wavelength range can be positioned a selected distance from the surface of the arm (i.e., the skin 160) so as to irradiate a desired area around the catheter insertion site 150 in an effective dose as shown in FIG. 1.

In general, the skin 160 surrounding the insertion site 150 can be exposed for a selected length of time. The exposure time can be controlled using a timer, for example, through the use of an electronic control module or other methods. In another embodiment, the exposure time can be controlled manually, e.g., through use of a switch, button, or other control that allows a caregiver to irradiate the target area for a selected amount of time.

In general, the area of the skin exposed to the radiation 140 can be chosen according to the type of catheter used, as well as the type of dressing used (if any), the presence of open sores, lesions, or other breaches of the skin (if any), and other considerations that can be determined by the user of the system 100 (e.g., a healthcare worker). For example, in the case of a single intravenous catheter, prepared under relatively sterile conditions and placed by an experienced medical provider, the caregiver may decide to irradiate a small area (e.g., 3-4 cm) around the insertion site to prevent the likelihood of infectious microorganism growth in that area. In another example having somewhat opposite circumstances, a patient may be delivered to a hospital after an automobile accident, where paramedics emergently inserted an intravenous catheter to reduce the likelihood of shock. In this case, where thorough sterilization techniques may have been secondary to stabilizing the victim, the irradiation area of the skin around the catheter insertion site 150 can be enlarged to encompass a greater area, e.g., 10-12 cm around the insertion site 150. Furthermore, in the latter case, the exposure time can be increased a desired amount to account for the increased risk of infection under the circumstances described.

In some embodiments, the light source 110 can be mounted in a preferred configuration and orientation so as to provide an effective dose of radiation to the treatment area. For example, the light source 110 can be mounted a selected distance from the patient's skin so as to provide reproducible exposure to a desired area of the body, e.g., a catheter insertion site. One suitable approach for this purpose includes using molded plastic components that attach to a body part (e.g., attach to an arm using a strap), while simultaneously providing a bridge or other frame component configured to secure the light source 110 in a preferred configuration to irradiate selected area(s) of the patient's skin. In another embodiment, the light source can be attached directly to the dressing in a configuration that directs the emitted light 140 toward the target area. In one example of such an embodiment, an array of LED lights capable of providing an effective dose of violet light to cause reduction in proliferation of microorganisms can be integrated into one side of a dressing using glues, adhesives, hook-and-loop fastening systems, cloths, or other methods that will be apparent to skilled artisans.

Figure 2:
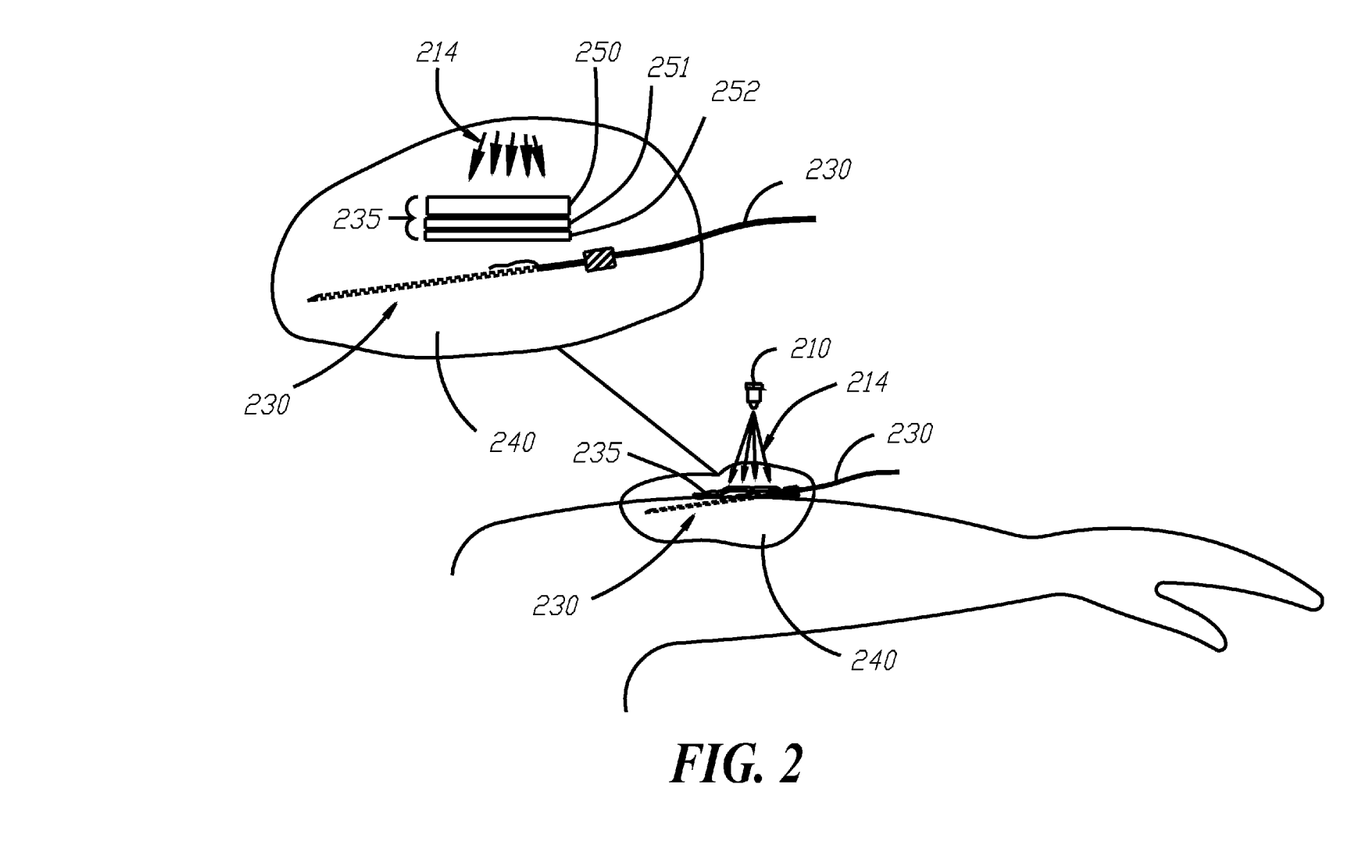
FIG. 2 shows a system for reducing the likelihood of infection, according to one embodiment.

Referring now to FIG. 2, a system for reducing the likelihood of infection is shown, according to one embodiment. This system, similar to the system shown and described with respect to FIG. 1, includes a light source 210 capable of producing an effective dose of violet light to reduce the likelihood of microorganism proliferation on a target area of the skin 240. A catheter 230 is shown inserted into the skin 240, where the dashed lined indicates the portion of the catheter under the skin layers.

The blow up region shows a dressing 235 having a plurality of layers, 250, 251, and 252 which can be the same or different materials. In one example, one of the layers (e.g., layer 250) is an acrylic sheet that is transparent to violet light; one of the layers (e.g., layer 251) includes a cotton or other absorbent material; and one of the layers, (e.g., layer 252) includes a gel layer. In this example, the light rays 214 can propagate through the layers to reach the skin layer 240 in an effective dose to reduce or prevent proliferation of microorganisms. It will be understood that the dressing 235 can include one or more layers of material as necessary to provide a desired treatment for the patient. For example, a burn victim may benefit from a dressing having a silver-containing gel layer in contact with their skin (e.g., layer 252) which covers the inserted catheter 230.

Figure 3A:
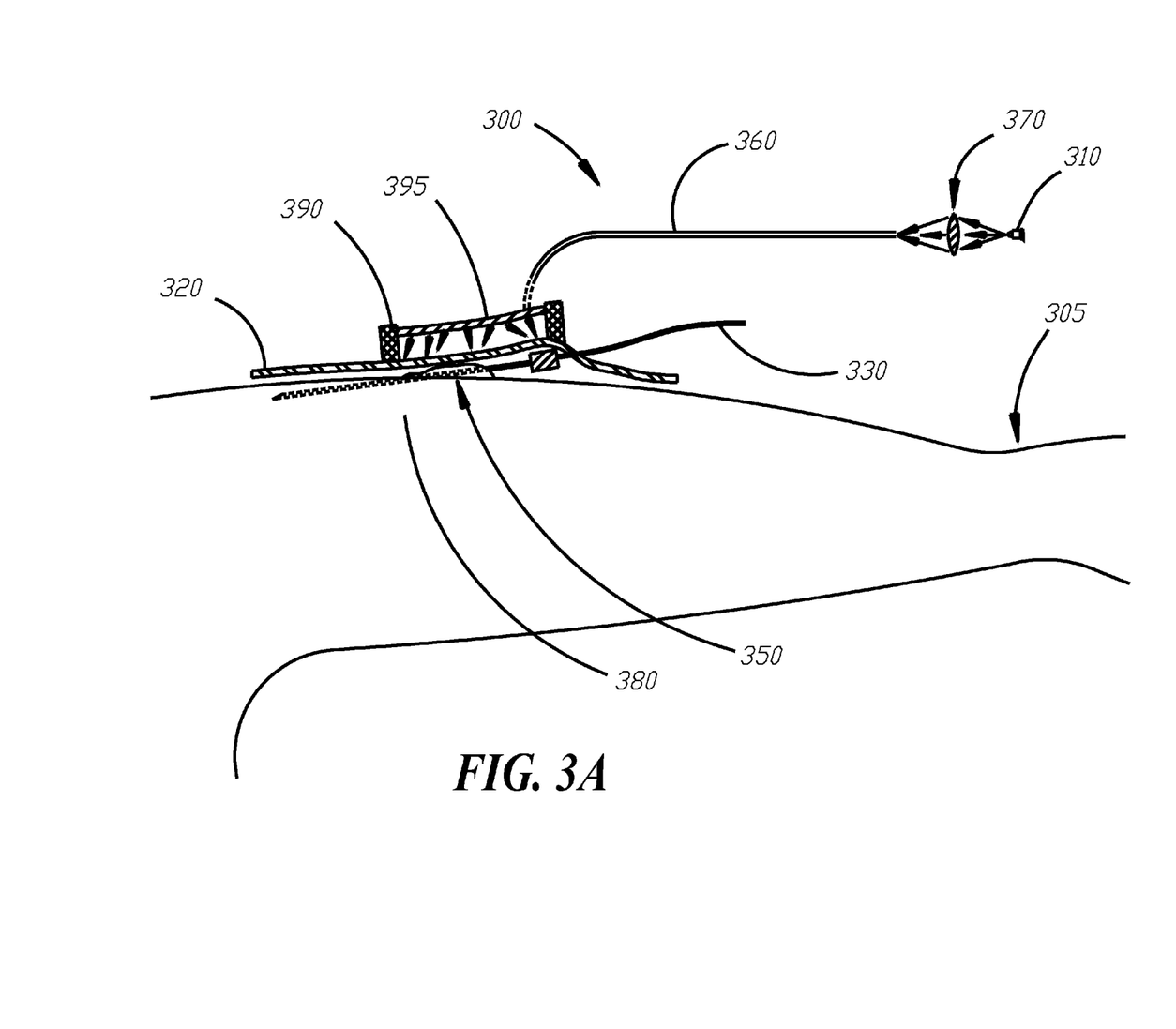
FIG. 3A shows a system for reducing the likelihood of infection, according to one embodiment.

Referring now to FIG. 3A, one embodiment of a system 300 for reducing the likelihood of infection is shown. Similar to the embodiment of FIG. 1, FIG. 3 shows a catheter 330 inserted into the skin 380 of a patient's arm 305 through an insertion site 350 (e.g., an incision in the skin produced by an IV needle). The insertion site 350 and surrounding area is covered by a dressing 320 that is at least partially transmissive with respect to violet light. In a preferred embodiment, the dressing 320 is an absorbent clear acrylic dressing sold under the Tegaderm brand (vide supra).

In this and other embodiments, violet light can be generated remotely by a light source 310, which can be a laser, diode, or other light source capable of producing an effective dose of violet light at the treatment site. The violet light can be carried by a waveguide 360, e.g., a fiber optic cable, to a dispersion optic 395 capable of dispersing the light from the fiber optic onto a desired area. It will be understood that the term "dispersion" as used herein, refers to increasing the irradiance area of the light from a source to a target, e.g., from the output end of a waveguide to a larger area on a patient's skin; the term does refer to the spatial or temporal separation of light into components of different wavelengths.

The dispersion optic 395 can be, in one example, a lens that causes divergence of the light from the confines of the cross-section of the waveguide 360 to a desired size (i.e., area). The lens can be made of any suitable material to perform this function, and various types of lenses may be used. For example, traditional curved dielectrics made of glass can de-focus or de-collimate the output of the waveguide to achieve irradiance over a desired area on the patient's skin. In another example, so-called "flat" lenses may be used, such as lenses that incorporate photonic crystals. In such an embodiment, light from the waveguide can be injected into a flat slab having photonic crystals that produce a negative index of refraction and cause the light to be emitted over a broad area. The injected light can spread over two-dimensional space within the slab; when applied to the insertion site 350, the slab can blanket the area with violet light. In yet another example, the dispersion optic 395 can be a Fresnel lens, which can be flexible to accommodate being placed on curved surfaces, such as the surface of a body part.

Figure 3B:
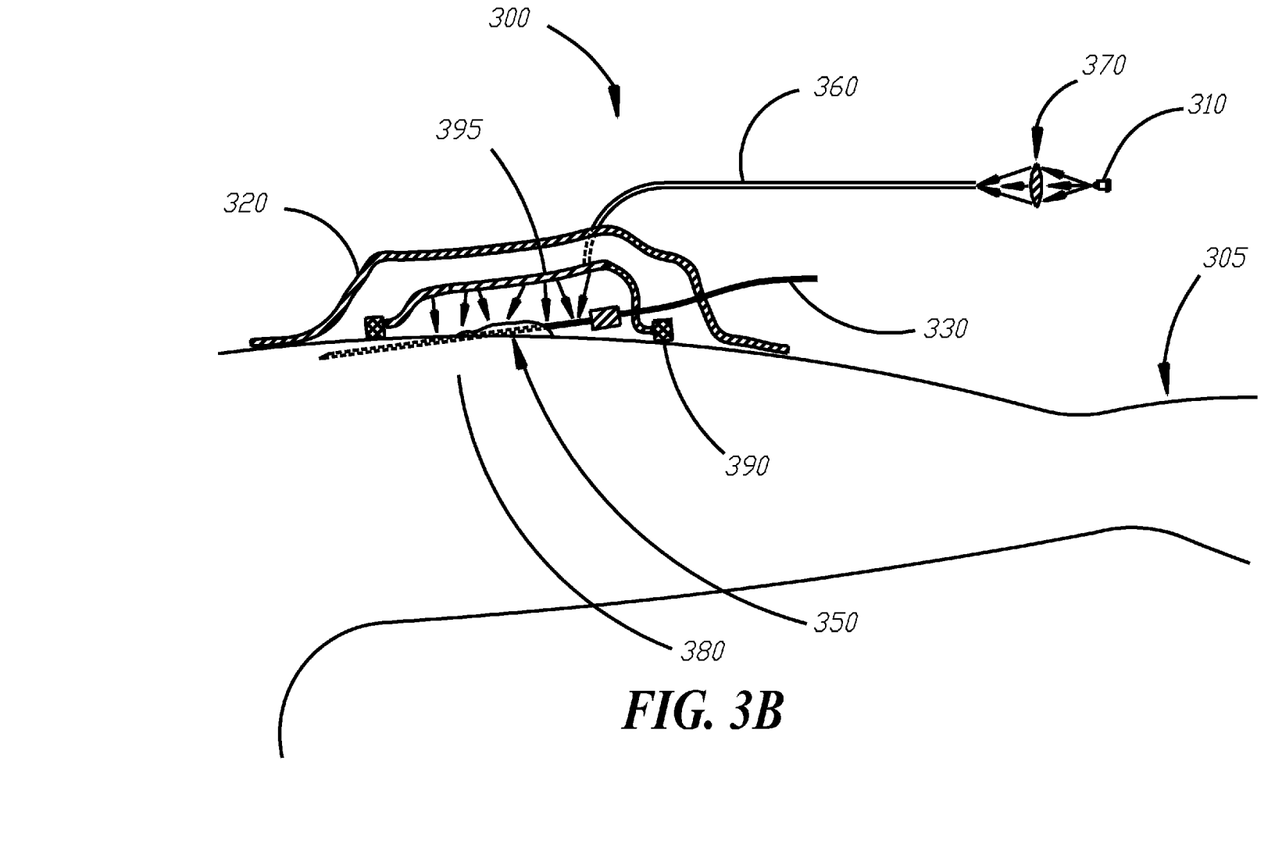
FIG. 3B shows an alternative arrangement of the system shown in FIG. 3A, according to one embodiment.

FIG. 3B shows an alternative arrangement of the system 300 shown in FIG. 3A, according to one embodiment. Here, the positions of the dispersion optic 395 and the dressing 320 are switched, i.e., the dispersion optic 395 is juxtaposed between the catheter 330 and a portion of the patient's skin 350, and the dressing 320. Compared to the embodiment shown in FIG. 3A, the arrangement shown in FIG. 3B can reduce or eliminate loss associated with light propagating through the dressing 320 and can result in increased irradiance to the target area. In this embodiment, the fiber optic 360 can extend through the dressing 320 and couple to the dispersion optic 395 using methods known in the optics art fields.

Referring now to FIGS. 3A and 3B, it will be understood that the type of dressing 320 used in these embodiments can be chosen according to preference. In a preferred approach, the dressing used in the embodiment shown in FIG. 3A includes a window capable of allowing violet light to pass therethrough, i.e., it is transmissive with respect to violet light; on the other hand, the dressing used in the embodiment shown in FIG. 3B can be an occlusive dressing, since its main purpose not to allow light to propagate therethrough, but instead to protect the underlying skin, catheter, and dispersion optic.

Figure 4:
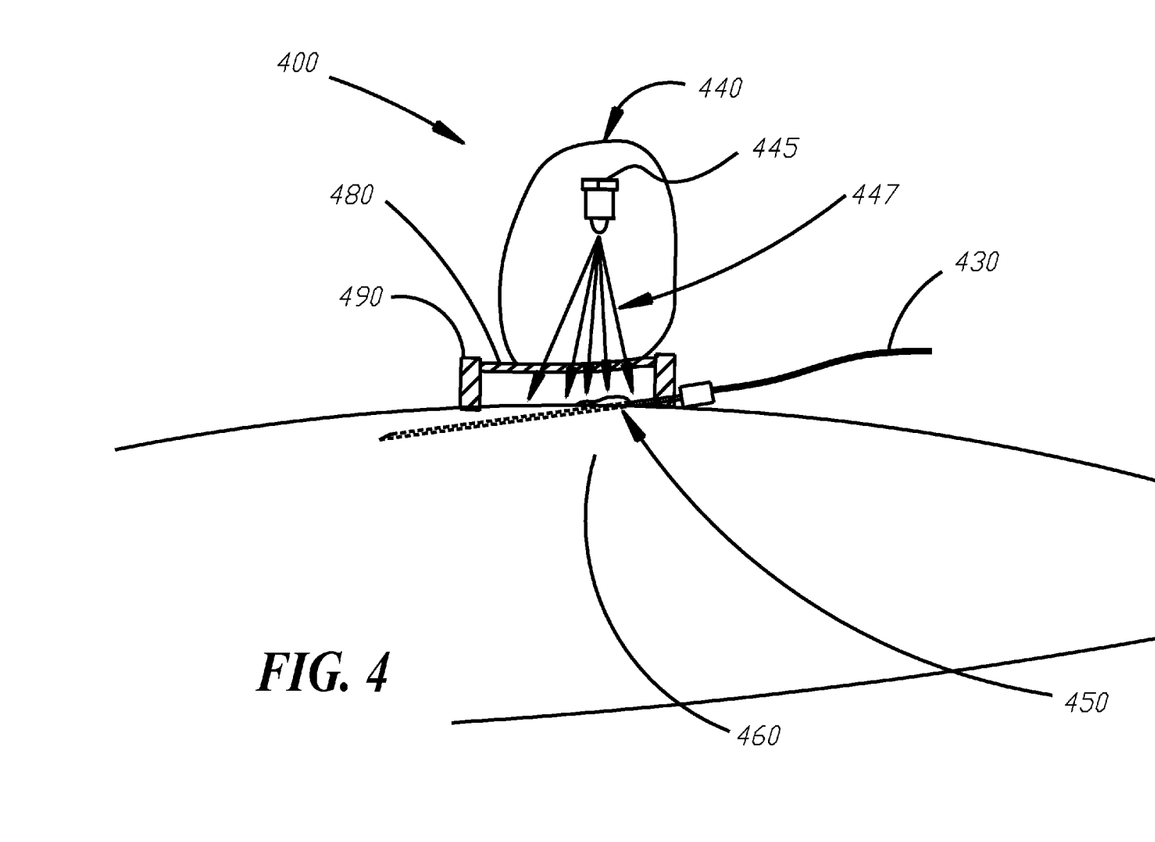
FIG. 4 shows a system for reducing the likelihood of infection at or near a catheter insertion site, according to one embodiment.

Referring now to FIG. 4, a system 400 for reducing the likelihood of infection at or near a catheter insertion site is shown, according to one embodiment. Here, similar to the embodiments described above, a catheter 430 is shown inserted into a patient's arm 460, e.g., subdermally, through an insertion site 450. A light source 445 capable of producing an effective dose of violet light 447 to cause reduction in proliferation of microorganisms at the target site is attached to a dressing 420. The dressing 420 is adhered to the patient's arm 460 through the use of an adhesive ring 490 disposed about the periphery of the dressing 420. In this embodiment, the light source 445 includes a power source so that the unit is self-contained, i.e., it does not require an external power source to produce the effective dose of violet light. Various self-contained power sources can be used that will be apparent to those skilled in the art of light-emitting diodes, for example, and includes, without limitation, batteries, capacitors, and the like.

Figure 5:
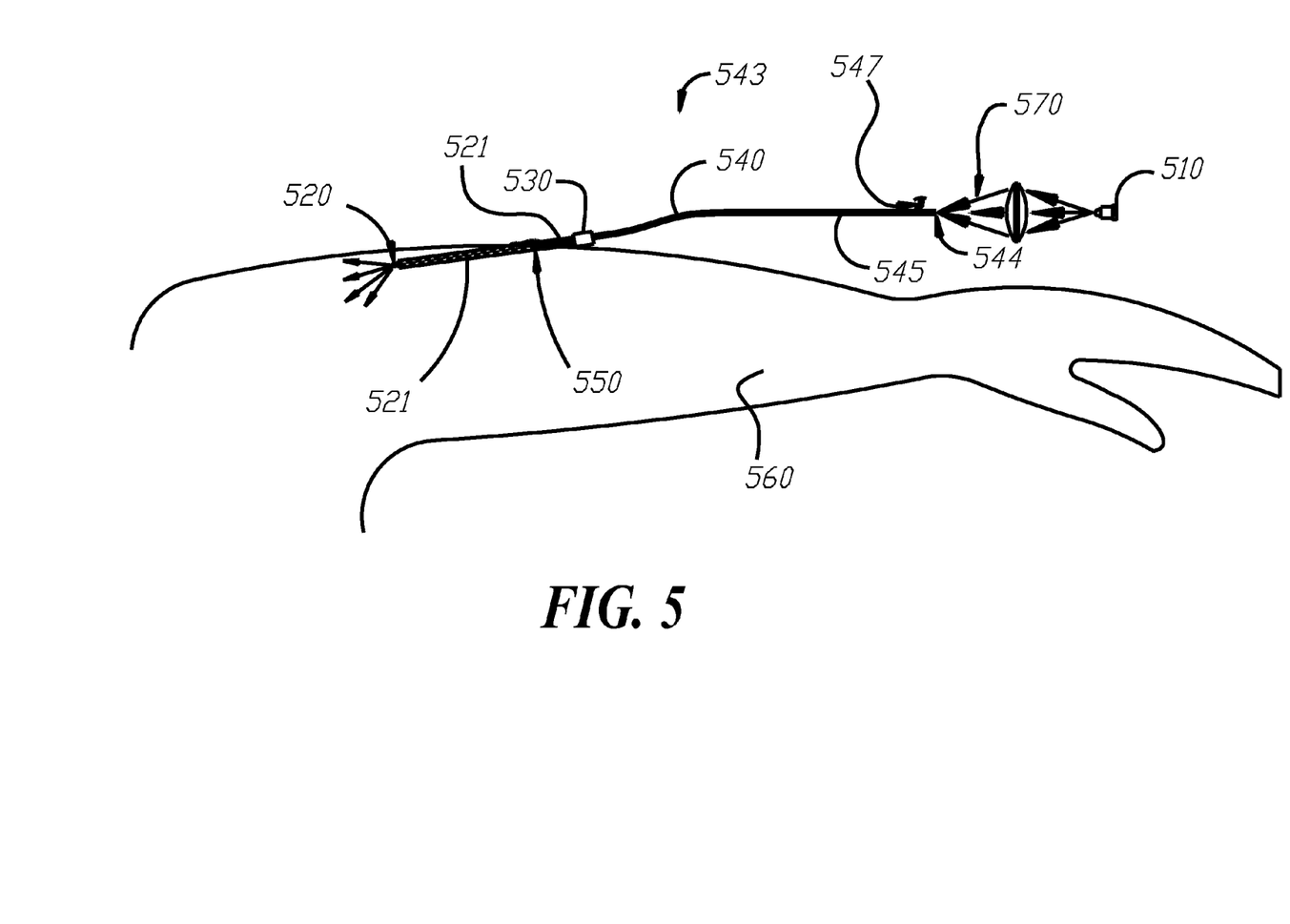
FIG. 5 shows a system for reducing the likelihood of infection at or near a catheter insertion site, according to one embodiment.

Referring now to FIG. 5, a system 500 for reducing the likelihood of infection related to catheter insertion is shown, according to one embodiment. The system 500 includes a light source 510 capable of producing light in the wavelength range of between about 385 nm and about 425 nm. Suitable light sources for this purpose include, without limitation, lasers, diodes, various types of lamps, excitable filaments, chemi- and electroluminescent materials, and fluorescent and phosphorescent materials, among others. The light output of the light source 510 can be directed into a waveguide 540 (e.g., a fiber optic) via one or more coupling optics 570; the type and configuration of the coupling optics 570 can be chosen according to the intended use and other factors, and the particular configuration will be known by those skilled in the art of fiber optics and light injection.

Figure 5A:
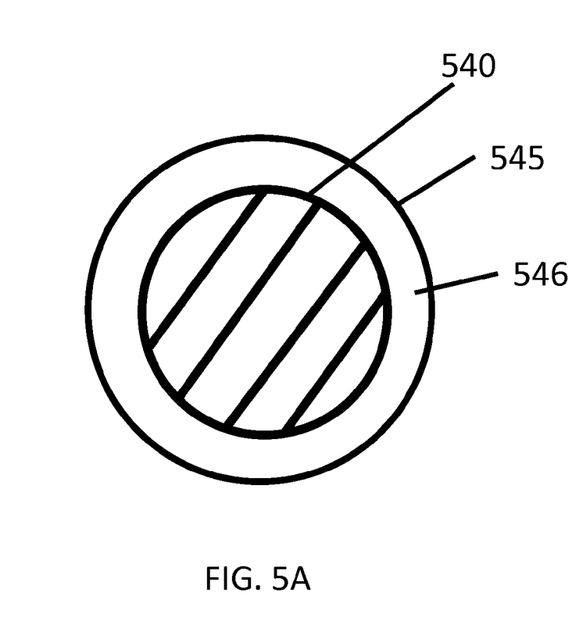
FIG. 5A shows a cross-sectional view of a terminal end of the catheter 543 described with respect to FIG. 5, according to one embodiment.

Referring to FIGS. 5 and 5A, in this embodiment, a portion of a catheter 543 includes a hollow, flexible sleeve 545 that houses the waveguide 540 therein; a void space (generally indicated by reference numeral 546) allows fluid to be transported within the catheter 543 between the waveguide 540 and the inner surface of the sleeve 545, between proximal 520 and distal 544 ends. In one embodiment, a distal end of the catheter 544 can be configured to receive the light output of the light source 510 in a distal end of the waveguide 540. The distal end can also include a fluid port 546 for inserting fluid into, or drawing fluid out of the catheter 543.

Referring back to FIG. 5, the catheter can be inserted into a patient's skin 560 at an insertion site 550 as previously described. The waveguide 540 can extend from the distal end to a proximal end 520 where the catheter can be configured to allow light to be emitted from the waveguide 540 into surrounding tissue for the purpose of reducing populations of infectious microorganisms that may be present due to catheterization. In one embodiment, the catheter 543 can include two sections that can be reversibly coupled. In such an embodiment, a union 530 allows an exterior portion of the catheter 543 to be joined to a proximal portion of the catheter 521 that comes into close proximity to, and, in some cases, penetrates the patient's dermal layers as shown in FIG. 5. In such an embodiment, the proximal portion of the catheter 521 can be configured to emit the light from the waveguide 540 along the length of the proximal portion 521, e.g., through use of a partially lossy waveguide, or by channeling portions of light from the central core waveguide 540 to the surface of the catheter 543. In this manner, the proximal portion of the catheter 521 can irradiate the surface of the patient's skin 560, the dermal layers, and the surrounding sub-dermal layers (not illustrated in FIG. 5 for clarity) with violet light for the purpose of reducing populations of infectious microorganisms. It will be understood in this and other embodiments that catheters of the type described herein can be inserted into biological lumens, such as a patient's bladder or gastrointestinal tract, for the purpose of reducing the likelihood of infection.

In general, the systems and methods described herein can be used to treat infectious biofilms. As those skilled in the medical arts will appreciate, biofilms composed of gram-positive or gram-negative bacteria, yeasts, or other organisms can originate from the patient's skin, exposure to contaminated medical equipment or healthcare workers, or other sources, and can be difficult to treat. In one approach, an infectious biofilm can be treated by exposing the biofilm to an effective dose of violet light to cause reduction in the proliferation of the infectious microorganism.

Figure 6:
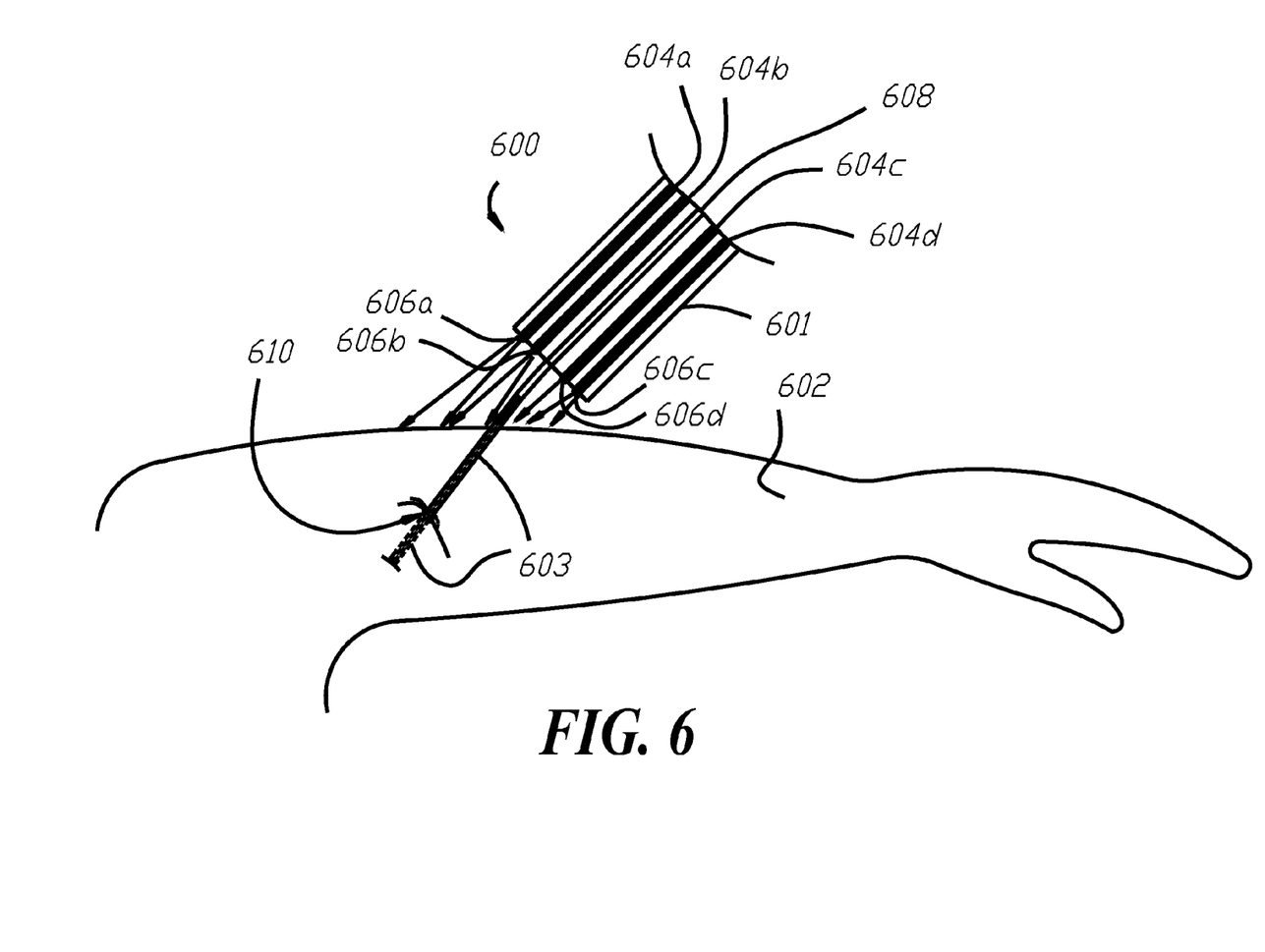
FIG. 6 shows a catheterization system, according to one embodiment.
Figure 6A:
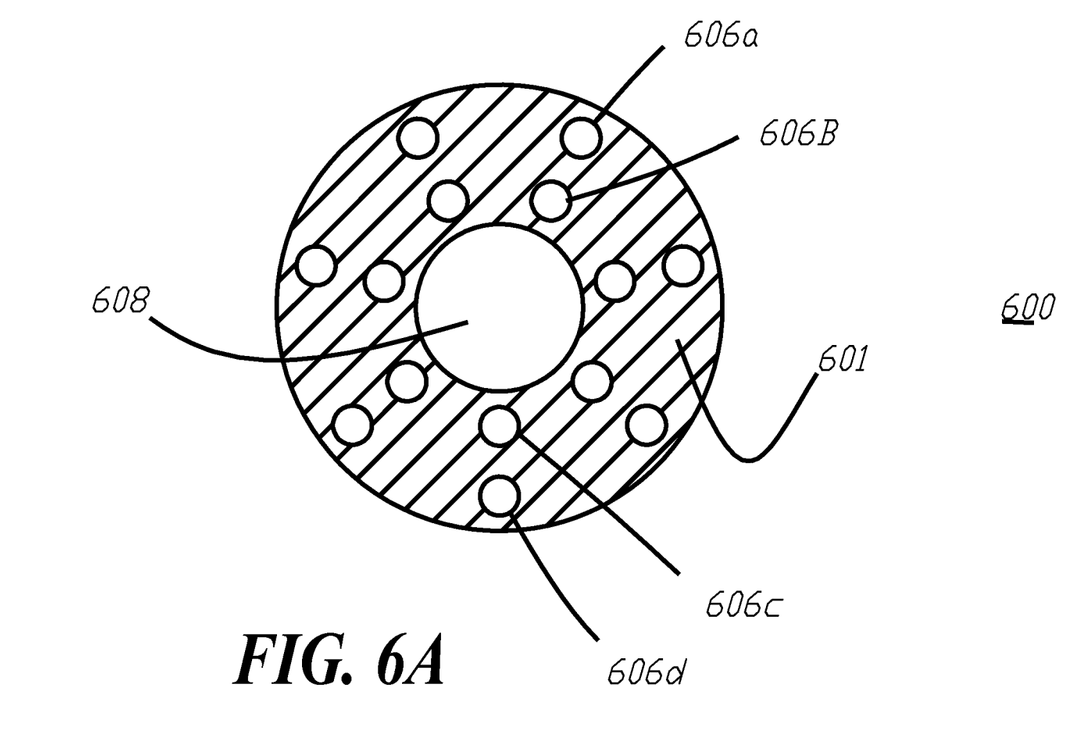
FIG. 6A shows a cross-sectional view of a terminal end of the catheter housing 601 described with respect to FIG. 6.

Referring now to FIGS. 6 and 6A, a catheter system 600 is shown. The catheter system is configured to reduce the likelihood of infection by delivering an effective dose of violet light to the surface of skin 602 at, and around the insertion site 610 of the catheter lumen 603, to reduce or inhibit the proliferation of infectious microorganisms. In this embodiment, the catheter system includes a housing 601, which can be flexible or rigid, that includes a central bore 608 for transporting fluids along the length of the housing 601. The catheter lumen 603 is a tube that extends the central bore 608 out of the housing 601 and allows fluid to flow between the proximal end of the housing 601 and the patient's blood stream in situations where the system 600 is being used for IV therapy. It will be understood that the catheter system 600 can be used for other treatments as well (vide supra).

The housing 601 includes one or more waveguides 604a-604d (e.g., fiber optics) arranged concentrically about the central bore 608. It will be understood that the configuration of waveguides and the central bore shown in FIGS. 6 and 6A is one of many possibilities, and other arrangements are equally contemplated. The waveguides 604a-604d extend from the proximal end (i.e., nearest to the patient's skin, as shown) to a distal end of the housing 601. The distal end of the housing is configured allow distal ends of the waveguides 604a-604d to receive the output of a light source (not shown in FIG. 6-6A for clarity) capable of producing an effective dose of violet light to reduce proliferation of microorganisms near the incision site 610. The distal end of the housing can also be configured to allow access to fluids in the central bore 608, so that fluids can be drawn from, or injected into, the patient.

The proximal end of the housing 601 houses the proximal terminal ends of the waveguides 604a-604d. In this embodiment, convex protuberances 606a-606d extend from the housing to produce a lens effect that causes the light emitted from the waveguide to disperse across a wider area, although in some embodiments this feature can be optional. The configuration of the waveguides is such that the area immediately surrounding the catheter insertion site 610 can be flooded with violet light. In this embodiment, the application of intense violet light can be focused near the area where the skin has been breached for catheterization. As previously described, this can cause a disruption in the ability of infectious microorganisms to reproduce, and thus reduce the likelihood of infection. In some circumstances, the catheter insertion site may be the area where the blood stream is vulnerable to outside infectious agents.

Figure 7:
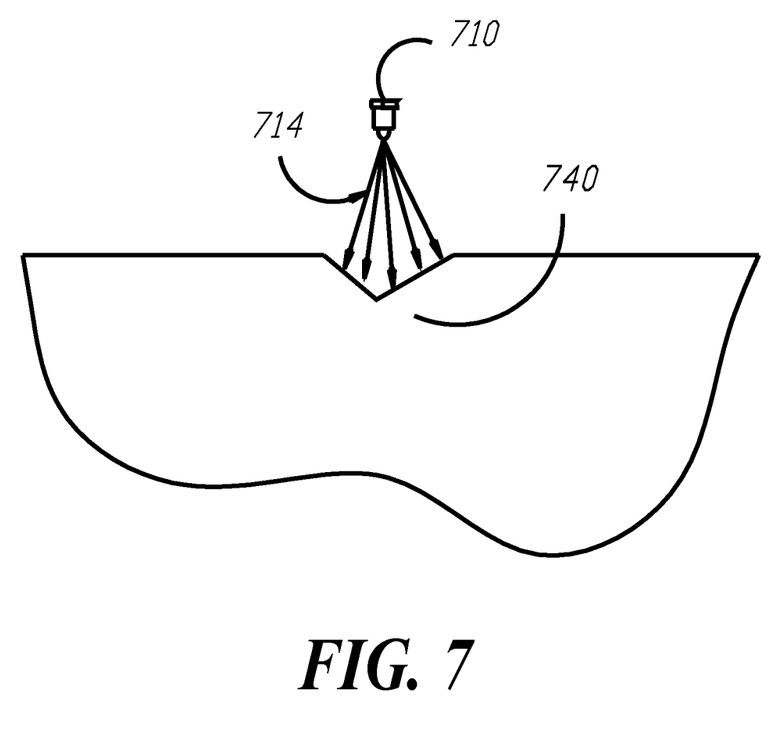
FIG. 7 shows a system for reducing the likelihood of microorganism growth, according to one embodiment.

Referring now to FIG. 7, a system for reducing the likelihood of microorganism proliferation is shown. A light source 710 provides output of an effective dose of violet light (indicated by reference numeral 714) which can be directed onto a surface 740. The surface 740 can be the surface of living tissue, similar to the embodiments described herein. In some embodiments, however, the surface can be non-living, for example, and without limitation, a surface of a piece of medical equipment, table- and countertops, processing areas, and other surfaces. In one embodiment, the surface 740 is a portion of processed food. Examples of processed foods include, without limitation, meats, such as steaks and other butchery cuts, eggs, breads, pastas, fish, confectionery items such as cakes and cookies, vegetables, and other foodstuffs. In another embodiment, the surface 740 is a portion of packaging used to package foods, such as a packaging tray for the foods just described.

In general, the system 700 can be used to reduce the likelihood of microorganism proliferation in and on foodstuffs by irradiating the target, i.e., the foodstuff or the packaging containing the foodstuff, with an effective dose of violet light sufficient to reduce or prevent microorganism reproduction. The system 700 can be used in, e.g., food processing facilities where foods are processed prior to distribution. For example, the system 700 can be used as part of a food processing system where foods are irradiated prior to packaging so that the proliferation of microorganisms on the food is reduced. Similarly, the system 700 can be used in food stores to reduce the likelihood of microorganism growth on foodstuffs, thereby prolonging the so-called shelf-life of the food. In one example, foods can be irradiated with an effective dose of violet light according to a schedule, e.g., every two days, to reduce microorganism growth.

Figure 8:
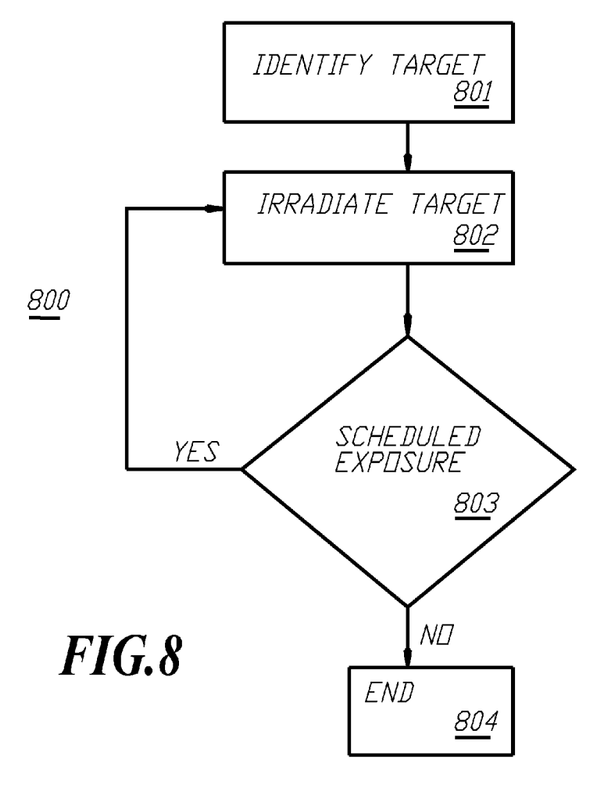
FIG. 8 shows steps of a method for reducing the likelihood of microorganism growth on a target surface, according to one embodiment.

In general, methods for reducing the likelihood of microorganism growth on a target surface are provided. Referring now to FIG. 8, the steps of a method 800 are shown, according to one embodiment. The method 800 can be used to reduce the likelihood of microorganism growth on a target surface, and, in some embodiments, within a host matrix. The method begins at step 801 by identifying a target. The target can be, in multiple embodiments, skin, tissue, muscle fiber, and other parts of living systems; one or more surfaces of medical equipment; one or more surfaces having the likelihood to become exposed to biological fluids, such as hospital beds, ambulance patient treatment areas, lavatory areas, etc.; catheters; food processing equipment; packaged food; and other surfaces. In a preferred embodiment, the target area is an area of living tissue immediately adjacent and surrounding a catheter insertion site, or other area where a body's barrier to infectious agents has been compromised.

Next, at step 802, the target area is irradiated with an effective dose of violet light so as to reduce the proliferation of microorganisms, e.g., infectious microorganisms. As described heretofore, "violet" light is generally considered to include light having a center wavelength of between about 385 nm and about 425 nm, e.g., light having a center wavelength of 385 nm, 390 nm, 395 nm, 400 nm, 401 nm, 402 nm, 403 nm, 404 nm, 405 nm, 406 nm, 407 nm, 408 nm, 409 nm, 410 nm, 415 nm, 420 nm, or 425 nm. "Irradiated" and "irradiating" as used herein, carries the common meaning and includes exposing the target surface with electromagnetic radiation from a light source. In general, the intensity of the violet light can be chosen according to user preference or circumstance to produce an effective dose sufficient to affect the proliferation of microorganisms. For example, a high intensity (high flux) can be used when an active microorganism population is witnessed, i.e., an infection is present, so as to affect the greatest population of the microorganisms as possible. Alternatively, a lesser intensity (lower flux) can be used as a preventive measure to keep lesser populations of microbes from reproducing and causing infection in a body.

The decision at step 803 can involve situations where irradiation is scheduled. "Scheduled irradiation" includes, e.g., irradiating a target surface on regular or otherwise timed or scheduled intervals. For example, in some circumstances, patients are given a catheter that may stay in the body for extended periods of time, e.g., 3-5 days. During this time, the catheter insertion site can be exposed to infectious microorganisms, which can increase the risk of bodily infection. Accordingly, a caregiver can set a timer, e.g., through an electronic control module, that activates the light source and causes the target surface to be exposed for a selected amount of time, at selected intervals. For example, the caregiver can set the timer to expose a patient's catheter insertion site for five minutes, every two hours. The intensity of the exposure can similarly be set and controlled for every exposure through the control module. If the answer to the "scheduled exposure?" question in step 803 is "yes," then the method returns to step 802 to expose the target surface; the loop between step 802 and step 803 iterates until the decision at step 803 is "no." The method then ends at step 804.

Figure 9:
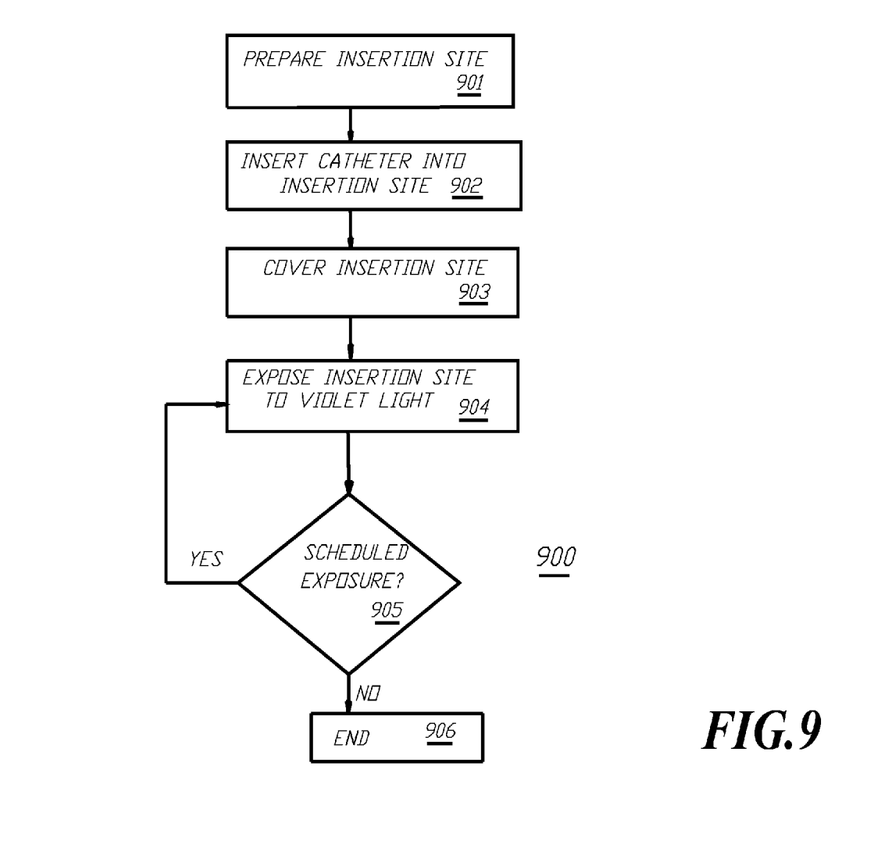
FIG. 9 shows steps of a method for reducing the likelihood of microorganism growth on a target surface, according to one embodiment.

Referring now to FIG. 9, a method 900 for reducing the likelihood of microorganism growth at or near catheter insertion sites is shown. This method 900 can be used, without limitation, in a variety of settings, including hospitals, veterinary clinics, triage units, emergency rooms, primary care clinics, ambulances, and in outside areas such as battlefields. This and other methods described herein can be practiced by, without limitation, physicians, veterinarians, ambulance crews, EMT's, firefighters, soldiers, or anyone placing a catheter within a living system. Beginning at step 901, the catheter insertion site is located, e.g., on the skin of a patient's arm or hand; while optional, in preferred embodiments, the site is disinfected to reduce the population of microbes that may be present, which is a practice those skilled in the art will recognize.

Next, at step 902, the catheter is inserted into the patient. In general, but without limitation, this step is often performed by inserting a needle through the patient's skin and into a blood vessel, such as in the case of IV therapy. A lumen (hollow, flexible tube) is then advanced into the blood vessel along the path defined by the needle; the needle is then withdrawn, leaving the lumen within the blood vessel. The lumen is generally connected to other catheter structures and tubing to allow fluids to be drawn out of, or inserted into, the patient. In some embodiments, such as the embodiment of FIG. 6, above, a portion of the catheter body includes one or more waveguides configured to irradiate the insertion site with violet light from a violet light source.

Next, at step 903, the insertion site is optionally covered to protect the catheter and the catheter insertion site. In some embodiments, the catheter and catheter insertion site can be covered with a dressing having a transparent window to allow caregivers to monitor the state of the catheter and catheter insertion site. In preferred embodiments, the dressing includes a transparent window having a flexible, clear acrylic window, and adhesive along its periphery allowing the covering to adhere to the patient's skin. Preferably, the material of the transparent window is transparent to violet light. Coverings sold under the Tegaderm brand (vide supra) are preferred.

Next, at step 904, the catheter insertion site and surrounding area is exposed to an effective dose of violet light to cause reduction in the proliferation of any microorganisms present. In general, the intensity of the violet light can be chosen according to circumstances as described with respect to the method of FIG. 8. In general, the insertion site can be exposed from a selected vantage point, e.g., from above, from the side, or in a "blanket" fashion, if, e.g., the light source is the type as described in FIGS. 3-3B.

Next, decision 905 asks whether the exposure is scheduled on a repeating basis. In some cases, a caregiver may decide to give the patient a single dose of radiation; in other cases, e.g., when the catheter is a "permcath" the caregiver may elect to administer repeating doses of radiation over a selected period of time. In the latter case, step 904 is repeated until the number of selected exposures has been reached.

A number of illustrative embodiments have been described. Nevertheless, it will be understood that various modifications may be made without departing from the spirit and scope of the various embodiments presented herein. For example, the concepts described herein can be applied toward other scenarios where microorganism growth and proliferation can be problematic. For example, microorganism growth is known to cause structural damage to building components such as wood framework and stucco. To combat this problem, light sources capable of producing an effective dose against microorganism reproduction can be placed in areas where microbes live, or have the capability of colonizing. In one embodiment, high-intensity LEDs can be placed in the framework of buildings as they are being constructed; the LEDs can be activated on a selected schedule (e.g., once a day) to reduce the likelihood of microorganism growth in areas that would otherwise be accessible only through demolition.

In one embodiment, the concepts, systems, and methods described herein can be applied to combating the problem of microorganism growth inside of fuel tanks, e.g., airliner fuel tanks. It is known that certain bacteria can degrade aluminum fuel tanks which can be costly to repair; likewise, it is known that certain bacteria can degrade fuels such as aviation fuel. Accordingly, light sources capable of producing an effective dose of violet light to interfere with microorganism reproduction can be installed in various types of tanks, e.g., fuel tanks. In such an approach, it can be advantageous for obvious reasons to use a light source that produces little heat, such as an LED, or utilize waveguides to carry violet light from a light source to the interior of the tank.

In one embodiment, the concepts, systems, and methods described herein can be used in the restaurant industry to reduce the likelihood of microorganism growth on cooking and eating surfaces.

In general, the effective dose of violet light to cause a reduction in the proliferation of a microorganism can be adjusted for different types of microorganisms.

Accordingly, other embodiments are within the scope of the following claims.

What is claimed is:
1. A system for reducing the likelihood of infection in a living system, comprising:

a solid-state light source configured to produce an effective dose of electromagnetic radiation in the violet portion of the electromagnetic spectrum so as to reduce the proliferation of microorganisms on a target surface, wherein said effective dose of electromagnetic radiation is delivered to said target surface via an optical fiber in optical communication with said light source; and an electronic control module configured to allow a user to toggle emission of said effective dose between on and off states.

2. The system of claim 1, wherein said microorganisms are one or more of: bacteria, fungi, or protist.

3. The system of claim 1, further comprising:
a support body capable of securing a distal end of said optical fiber proximate to said target surface in an orientation suitable to project said electromagnetic radiation onto said target surface.

4. The system of claim 3, wherein said target surface is a selected portion of skin, tissue, bone, muscle fiber, lumen, or organ.

5. The system of claim 1, wherein said solid-state light source is configured for producing said effective dose of electromagnetic radiation such that it is capable of transmission through a protective dressing comprising polyurethane and onto said target surface while minimizing the likelihood of causing damage to cells of said target surface.

6. The system of claim 5, wherein said dressing comprises one or more layers of a solid, liquid, or gel material that is at least partially transmissive with respect to said electromagnetic radiation and formulated to provide a therapeutic effect to said target surface.

7. A system for reducing the likelihood of infection at or near a catheterization site, comprising:
a solid-state light source capable of producing an effective dose of electromagnetic radiation sufficient to reduce proliferation of a population of infectious microorganisms, wherein said electromagnetic radiation has a center wavelength between about 385 nm and about 425 nm; and a catheter at least partially engaged with at least one optical fiber configured to transmit said effective dose of electromagnetic radiation from a proximal end of said waveguide to a distal end of said waveguide, wherein said distal end of said waveguide is capable of projecting said radiation onto a target surface at or near said catheterization site.

8. The system of claim 7, wherein said optical fiber is at least partially embedded in said catheter.

9. The system of claim 8, wherein said elongate catheter is capable of transporting fluids into and out of an animal body.

10. The system of claim 7, wherein said system is configured such that said effective dose is capable of being transmitted through a protective dressing formed primarily of polyurethane.

11. The system of claim 10, wherein said protective dressing comprises a compound formulated to prevent infections in animals.

12. The system of claim 7, further comprising an electronic control module configured to allow user input for controlling at least one of: exposure time, exposure intensity, and time between repeated exposures of said electromagnetic radiation onto said catheter insertion site.

13. A method for reducing the likelihood of infection in a living system, comprising:
providing a light source capable of producing an effective dose of electromagnetic radiation sufficient to cause a reduction in proliferation of a microorganism and having a center wavelength between about 385 nm and about 425 nm; and providing an elongate catheter, comprising:
a housing having a bore extending therethrough from a proximal catheter end to a distal catheter end,
an elongate lumen in fluid communication with said bore extending from said proximal catheter end and configured to be inserted into tissue of an animal body at a catheter insertion site; and
one or more optical fibers at least partially engaged with said elongate catheter, wherein a distal end of said waveguide is configured to receive said electromagnetic radiation, and a proximal end of said waveguide is configured to project said electromagnetic radiation about said catheter insertion site to cause necrosis in said infectious microorganism.

14. The method of claim 13, wherein said light source comprises a laser, diode, excitable gas, or filament.

15. The method of claim 13, wherein said distal end of said waveguide is configured to project said effective dose within a tissue or organ of said living system.

16. The method of claim 13, further comprising providing a therapeutic dressing that is substantially transparent to said electromagnetic radiation and configured to fix said proximal catheter end proximal to said catheter insertion site.

17. The method of claim 13, wherein said light source is configured to provide controllable effective doses of said electromagnetic radiation for a selected exposure period over a selected period of time to said catheter insertion site.

18. The method of claim 13, wherein said effective dose is determined based on the type of said infectious microorganism(s) capable of causing said infection.

* * * * *